Figure 1:
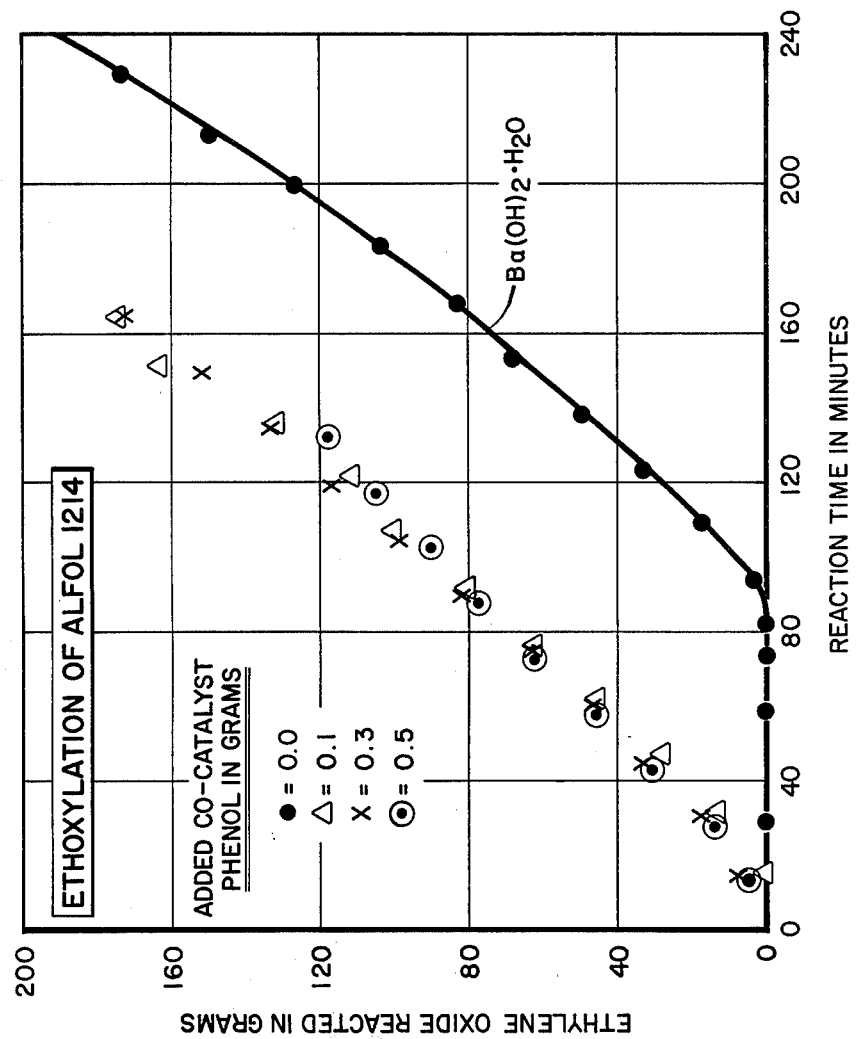

United States Patent [19]

Yang et al.

[11] 4,210,764
[45] Jul. 1, 1980

[54] BARIUM OXIDE/CRESYLIC ACID CATALYZED ETHOXYLATION

[75] Inventors: Kang Yang; Gerald L. Nield; Paul H. Washecheck, all of Ponca City, Okla.

[73] Assignee: Conoco, Inc., Ponca City, Okla.

[21] Appl. No.: 36,273

[22] Filed: May 4, 1979

[51] Int. Cl.$^2$ .................. C07C 41/02; C07C 41/10
[52] U.S. Cl. ........................ 568/618; 568/678
[58] Field of Search ................. 568/618, 678

[56] References Cited

U.S. PATENT DOCUMENTS

| | | | |
|---|---|---|---|
| 3,475,499 | 10/1967 | Winnich | 568/618 |
| 3,644,535 | 2/1972 | Batty et al. | 568/618 |

*Primary Examiner*—Howard T. Mars
*Attorney, Agent, or Firm*—Cortlan R. Schupbach, Jr.

[57] ABSTRACT

Cresylic acid (phenol or alkylated phenols) is used to promote barium oxide or hydroxide which is used as an ethoxylation catalyst for the reaction of ethylene oxide and alkanols of all classes. The reaction is carried out at temperatures of from about 150° to about 200° C. to yield the ethoxylated product. The product obtained has a very narrow high adduct distribution with low levels of by-products and unreacted free alcohols. Calcium and magnesium oxides show negligible catalytic effect.

10 Claims, 4 Drawing Figures

BARIUM OXIDE/CRESYLIC ACID CATALYZED ETHOXYLATION

This invention relates to the production of ethoxylated alcohols by reacting said alcohols with ethylene oxide. More particularly, this invention relates to the production of ethoxylated alcohols by reacting said alcohols in the presence of a barium catalyst promoted by phenol or alkylated phenols.

The general reaction of alcohols and ethylene oxide to form ethoxylated alcohols or ethylene oxide adducts has long been known and practiced on a commercial scale. For example, these ethylene oxide adducts have been used as detergents and cleaning agents, domestic and industrial laundry detergents, detergent builders, polishes, sanitizers and dry cleaning materials. Other users include the pulp and paper industry and the fiber industry. These materials are especially adapted to these uses since they have functional properties such as wetting power, foaming, emulsifying and dispersing abilities as well as solubilization and detergent abilities to facilitate their use.

Much literature is available in the general area of ethoxylation of alcohols. Many references are also available relating to the catalytic ability of various materials and the mechanism and kinetics of these reactions. For example, French Pat. No. 1,365,945 teaches the use of compounds containing an active hydrogen atom reacted with ethylene oxide in the presence of an alkali metal base. Acidic catalysts in general are also known. However, the ethoxylation of alcohols inevitably produces a distribution of various adducts. For example, in surfactant applications, an adduct with too few ethylene oxide molecules is not effective because of poor solubility, while an adduct with too many ethylene oxide molecules is likewise undesirable because surface tension reduction per unit mass decreases drastically with increasing molecular weight. Thus it has long been essential to produce and use ethoxylates with a sharp distribution in the desired mole adduct range (5 to 10 usually) if possible. Acid catalyzed reactions such as that described above produce such ethoxylates but these catalysts produce harmful side products such as dioxanes which must be separated and removed prior to use.

Russian Pat. No. 523,074 teaches that alkali metals and various carbonates can be used to catalyze this reaction. The side product formation in these base catalyzed reactions is very low but in base-catalyzed reactions the adduct distribution is undesirably broad such that a large proportion of the product obtained is not useful.

Representative of but not exhaustive of the art in this area is U.S. Pat. No. 3,328,467 which describes the use of zeolites and modified zeolites as catalysts in ethoxylation reactions. French Pat. No. 1,557,407 uses triethyl oxonium fluoroborate to catalyze such reactions. Indeed, the art abounds with references to alkali metal hydroxides such as sodium and potassium hydroxide, tertiary amines and sodium metal. German Offenlegungsschrift No. 2,639,564 teaches polyalkylation of active hydrogen compounds in the presence of sodium fluoroborate or perchlorates of metals such as magnesium, calcium, manganese, or zinc. U.S. Pat. No. 3,969,417 uses tertiary oxonium salts as a catalyst.

U.S. Pat. No. 3,830,850 describes adding sodium, potassium, lithium, rubidium, cesium, calcium, barium, or strontium to condense phenols with formaldehyde then adding ethylene oxide in an ethoxylation reaction. However, all these materials have the disadvantages described and set forth above.

Great benefit would be provided by a catalyst system which provides the low by-product levels of base catalysts yet has the narrow distribution of the preferred mole adducts obtained from acid catalysts. Such a catalyst which would promote the narrowing of the product distribution curve would contribute significantly to the intrinsic value of the ethoxylate produced. Such a catalyst is described in U.S. application Ser. No. 916,421, filed June 6, 1978. However, this catalyst has an induction period ranging up to about 20 minutes at 178° C. and produces from 1 to 2 percent polyethylene glycol in the product which is still undesirably large.

It is therefore an object of the present invention to provide a catalyst system which will yield a narrow, high mole adduct distribution from the reaction of alcohols of all classes with ethylene oxide while providing low levels of undesirable by-products and unreacted free alcohols, yet provide a reaction which is immediately effective with reduced induction period. Other objects will become apparent to those skilled in this art as the description proceeds.

It has now been discovered according to the instant invention that ethoxylation of all classes of alkanols can be carried out in the presence of barium oxide, hydrated barium oxides and other barium bases such as barium metal to provide a narrow distribution of ethylene oxide adducts while yielding a very low level of free alcohols and undesirable by-products while simultaneously avoiding the previously noticed induction period before the ethoxylation reaction begins by adding to the catalyst system an effective amount of phenol, alkylated phenols or mixtures of these, said phenols having the general formula

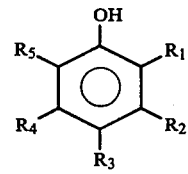

wherein $R_1$, $R_2$, $R_3$, $R_4$, and $R_5$ are, independently, hydrogen or an alkyl group containing from 1 to 10 carbon atoms.

The instant invention describes a method for the ethoxylation of alcohols comprising contacting said alcohols with ethylene oxide in the presence of barium oxide catalysts together with an effective amount of phenol or alkyl substituted phenol or mixtures of these to promote reaction. The instant invention can be carried out at temperatures of from about 90° C. to about 260° C. Normally, the alcohols reacted under the process of the instant invention will contain from about 4 to about 24 carbon atoms but alcohols containing from about 10 to about 18 carbon atoms are those most used for commercial purposes. The process of the instant invention can be carried out at ambient pressures. However, pressures up to 100 pounds per square inch gauge (psig) can also be used, but pressures below 60 pounds per square inch gauge are preferred.

Representative examples of materials which promote barium oxide catalysts are phenol, ortho cresol, metacresol paracresol, 2,4-dialkylphenol, 2,5-dialkylphenol, nonylphenol and octylphenol.

While pressure or lack of pressure is not a detriment to the process of the instant invention, normally a pressure of up to about 100 pounds per square inch gauge (psig) can be used. Preferred pressures are from about 10 to about 50 psig. However, it must be realized that the reaction can be carried out at a lower pressure or at pressures above 100 psig if desired. It is simply more convenient to carry out the reaction in the pressure range of from about atmospheric to 100 psig.

The instant invention is normally carried out at temperatures of from about 120° to 260° C. However, for practical purposes, commercial operations will normally be carried out in the temperature range of from about 150° C. to about 250° C. Temperatures in the range of from 160° C. to about 190° C. are most preferred.

Reaction products can have any desired content of ethylene oxide, but will normally range from about 30 to about 80% content of ethylene oxide (EO) based on weight. However, for most purposes, the content of ethylene oxide will range from about 40% to about 70% by weight. The amount of EO present in the reaction is not critical other than the minimum amount necessary to provide sufficient units to reach the mole adduct level desired for the alcohol being reacted.

The barium oxide catalyst of the instant invention is a basic catalyst which provides a sharp distribution as to the mole adducts formed, while reducing greatly the amount of unreacted free alcohols and undesirable by-products normally found in sharp distribution reactions. Barium oxide used alone appears to be unique, since tests carried out with metal oxides of calcium, magnesium, and strontium failed to reveal any significant ethoxylation activity. The instant invention adds to this barium oxide catalyst an effective amount of phenol, substituted phenol or mixtures of these in order to further reduce by-product reactions and to reduce or eliminate the induction period necessary for ethoxylation to begin.

For the purposes of the instant invention, the barium catalyst can be barium oxide alone, barium, metal, barium hydroxide, and barium hydroxide hydrates. Any of these barium compounds are effective in the process of the instant invention and are extremely effective when used with phenol or substituted phenol co-catalyst in an effective amount. When used, these catalyst mixtures can be used in any desired quantity. The larger the quantity used, the more quickly the reaction goes to completion, although larger quantities do not appear to significantly alter the distribution obtained. However, for practical purposes, normally from about 0.1 to about 0.5 weight percent barium catalyst based upon the weight of the alcohols to be reacted would be present in the reaction. The amount of phenol or substituted phenol or mixtures of these which would be present with the barium catalyst is generally an effective amount. The larger the amount of phenol, substituted phenol, or mixtures of these added to the reaction, the shorter the induction period and the lower the amount of by-products formed. These effects of the co-catalysts become significant at about 0.1% by weight based upon the weight of the alcohol to be reacted, and appear to increase with the increasing amounts of phenol or substituted phenol co-catalyst added, although it is logical to expect an upper limit after which the amount of co-catalyst present will produce no additional benefits.

Normally, these materials will be added to the barium catalyst in amounts ranging from 0.1 to about 2% by weight based upon the weight of the alcohol, although amounts ranging from about 0.15 to about 1.5 are preferred and amounts from about 0.3 to 0.8% by weight based on the weight of the alcohol to be reacted is most preferred. However, it is very apparent that these limits can be varied substantially since the co-catalyst is effective at all levels.

Representative examples of barium containing catalysts are BaO, Ba(OH)$_2$ and Ba(OH)$_2$.X H$_2$O where X represents the number of water molecules present. X is not a critical number.

While the instant invention is effective with all classes of alkanols, both primary, secondary, tertiary, linear and branched, linear and branched primary alkanols are the most commonly used alcohols and are the preferred alcohols of the instant invention. Representative examples of such alcohols are those derived by hydrogenation of natural fats and oils, such as CO and TA alcohols, trademark of and sold by Proctor and Gamble Co., such as CO-1214N alcohol, CO 1618 alcohol, and TA 1618 alcohol, and ADOL alcohols, trademark of and sold by Ashland Oil Co., such as ADOL 54 alcohol, ADOL 61 alcohol, ADOL 64 alcohol, ADOL 60 alcohol, and ADOL 66 alcohol. Alcohols produced by Ziegler chemistry can also be ethoxylated. Examples of these alcohols are ALFOL alcohols, trademark of and sold by Continental Oil Co., such as ALFOL 1012 alcohol, ALFOL 1214 alcohol, ALFOL 1412 alcohol, ALFOL 1618 alcohol, ALFOL 1620 alcohol, and EPAL alcohols, trademark of and sold by Ethyl Chemical Co., such as EPAL 1012 alcohol, EPAL 1214 alcohol, EPAL 1418 alcohol. The invention is extremely useful for oxo alcohols (hydroformylation) produced from olefins. Examples of such alcohols are NEODOL alcohols, trademark of and sold by Shell Oil Co., such as NEODOL 23 alcohol, NEODOL 25 alcohol, NEODOL 1418 alcohol; TERGITOL, trademark of Union Carbide Corp, such as TERGITOL-L 125 alcohol; LIAL alcohols, trademark of and sold by Liquichimica Co., such as LIAL 125; and isodecyl and tridecyl alcohols, sold by Exxon Corp., such as isodecyl alcohol and tridecyl alcohol. Guerbet alcohols can also be ethoxylated. Representative examples of these alcohols are STANDAMUL alcohols, trademark of and sold by Henkel Chemical Co., such as STANDAMUL GT-12 alcohol, STANDAMUL GT-16 alcohol, STANDAMUL GT-20 alcohol, STANDAMUL GT-1620 alcohol. Secondary alcohols can also be used, such as TERGITOL 15 alcohol, trademark of and sold by Union Carbide Corporation.

Generally, useable alcohols include 1-decanol; 1-undecanol; 1-dodecanol; 1-tridecanol; 1-tetradecanol; 1-pentadecanol; 1-hexadecanol; 1-heptadecanol; 1-octadecanol; 1-nonadecanol; 1-eicosanol; 1-dicosanol; 2-methyl-1-undecanol; 2-propyl-1-nonanol; 2-butyl-1-octanol; 2-methyl-1-tridecanol; 2-ethyl-1-dodecanol; 2-propyl-1-undecanol; 2-butyl-1-decanol; 2-pentyl-1-nonanol; 2-hexyl-1-octanol; 2-methyl-1-pentadecanol; 2-ethyl-1-tetradecanol; 2-propyl-1-tridecanol; 2-butyl-1-dodecanol; 2-pentyl-1-undecanol; 2-hexyl-1-decanol; 2-heptyl-1-decanol; 2-hexyl-1-nonanol; 2-octyl-1-octanol; 2-methyl-1-heptadecanol; 2-ethyl-1-hexadecanol; 2-propyl-1-pentadecanol; 2-butyl-1-tetradecanol; 2-pentyl-1-tridecanol; 2-hexyl-1-dodecanol; 2-octyl-1-decanol; 2-nonyl-1-nonanol; 2-dodecanol; 3-dodecanol; 4-dodecanol; 5-dodecanol; 6-dodecanol;

2-tetradecanol; 3-tetradecanol; 4-tetradecanol; 5-tetradecanol; 6-tetradecanol; 7-tetradecanol; 2-hexadecanol; 3-hexadecanol; 4-hexadecanol; 5-hexadecanol; 6-hexadecanol; 7-hexadecanol; 8-hexadecanol; 2-octadecanol; 3-octadecanol; 4-octadecanol; 5-octadecanol; 6-octadecanol; 7-octadecanol; 8-octadecanol; 9-octadecanol; 9-octadecanol; 2,4,6-trimethyl-1-heptanol; 2,4,6,8-tetramethyl-1-nonanol; 3,5,5-trimethyl-1-hexanol; 3,5,5,7,7-pentamethyl-1-octanol; 3-butyl-1-nonanol; 3-butyl-1-undecanol; 3-hexyl-1-undecanol; 3-hexyl-1-tridecanol; 3-octyl-1-tridecanol; 2-methyl-2-undecanol; 3-methyl-3-undecanol; 4-methyl-4-undecanol; 2-methyl-2-tridecanol; 3-methyl-3-tridecanol; 4-methyl-3-tridecanol; 4-methyl-4-tridecanol; 3-ethyl-3-decanol; 3-ethyl-3-dodecanol; 2,4,6,8-tetramethyl-2-nonanol; 2-methyl-3-undecanol; 2-methyl-4-undecanol; 4-methyl-2-undecanol; 5-methyl-2-undecanol; 4-ethyl-2-decanol; 4-ethyl-3-decanol.

Generally, the treatment of alcohols with ethylene oxide yields a non-ionic detergent since hydrogen bonding to the numerous oxygen atoms makes the polyether end of the molecule water soluble. Alternatively, the ethoxylates can be converted into sulfates and used in the form of alkali metal salts.

The instant invention thus provides for the production of highly efficient alcohol ethoxylates from primary, secondary, and tertiary branch chain and straight chain alcohols, particularly alkanols, in a novel, highly unexpected manner. The alcohols normally have from about 4 to about 20 carbon atoms. The reaction products are useful as non-ionic surface active agents with high wetting powers and are composed of mixtures of mono-alkyl ethers of polyethylene glycol.

Thus in the preferred form in the instant invention, ethylene oxide is reacted with a branched chain and a straight chain higher alkanol in the presence of barium oxide, barium hydroxide, or other barium bases promoted by an effective amount of a cresylic acid which is composed of phenols, alkyl substituted phenols, or mixtures of these.

The invention is more concretely described with reference to the examples below wherein all parts and percentages are by weight unless otherwise specified. The examples are provided to illustrate the instant invention and not to limit it.

EXAMPLE 1

All examples were carried out in a stainless steel reactor (having a magnetic stirrer) and utilized 120 grams of a 12 to 14 carbon atom alcohol (ALFOL 1214 alcohol, Trademark of and sold by Continental Oil Company), 0.3 grams barium hydroxide.$H_2O$, and 0.3 grams phenol. After purging with nitrogen at 500 cubic centimeters per minute for 30 minutes at 150° C. 180 grams of ethylene oxide was allowed to react at 178° C. and 40 psig ethylene oxide pressure. The induction period was 2 minutes with a total reaction time of 80 minutes. Barium was removed as $BaSO_4$ by neutralization with aqueous $H_2SO_4$, followed by centrifugation. The ethoxylate produced contained 0.25 weight percent polyethylene glycol and had a 55° F. pour point. Unreacted free alcohol was 1.4%.

EXAMPLE 2

As a comparative example to Example 1, Example 1 was repeated several times without adding phenols to the reaction mixture. The average induction time for these examples was 20 minutes. The products contained 1 to 2% polyethylene glycol and had a pour point ranging from 60° to 65° F. Unreacted free alcohol was 1.3 weight percent.

EXAMPLE 3

A reaction exactly as described in Example 1 was carried out with the exception that phenol was replaced by orthocresol (0.35 grams) and in a second experiment nonyl phenol (0.90 grams). In each case the induction period was 2 minutes. The products contained 0.6% polyethylene glycol and had 60° F. pour points.

EXAMPLE 4

An experiment was carried out exactly as described in Example 1 except that barium hydroxide.$H_2O$ was replaced by calcium hydroxide (0.3 grams). No reaction occurred. At this point, 0.5 grams of phenol was added to the reaction mixture. At the end of 2 hours no ethoxylation had occurred.

EXAMPLE 5

Several experiments were carried out as described in Example 1 except that the reaction temperature was 150° C. and the amount of phenol added was varied from 0.1 g to 0.5 g. FIG. 1 graphically illustrates the results of these experiments, where the reaction induction period is reduced from more than 80 minutes to less than 20 minutes. In all figures, the vertical axis represents the total grams of ethylene oxide (EO) reacted, and the horizontal axis shows the reaction time in minutes. The reduction in induction period is readily apparent in FIG. 1.

EXAMPLE 6

Figure 2:
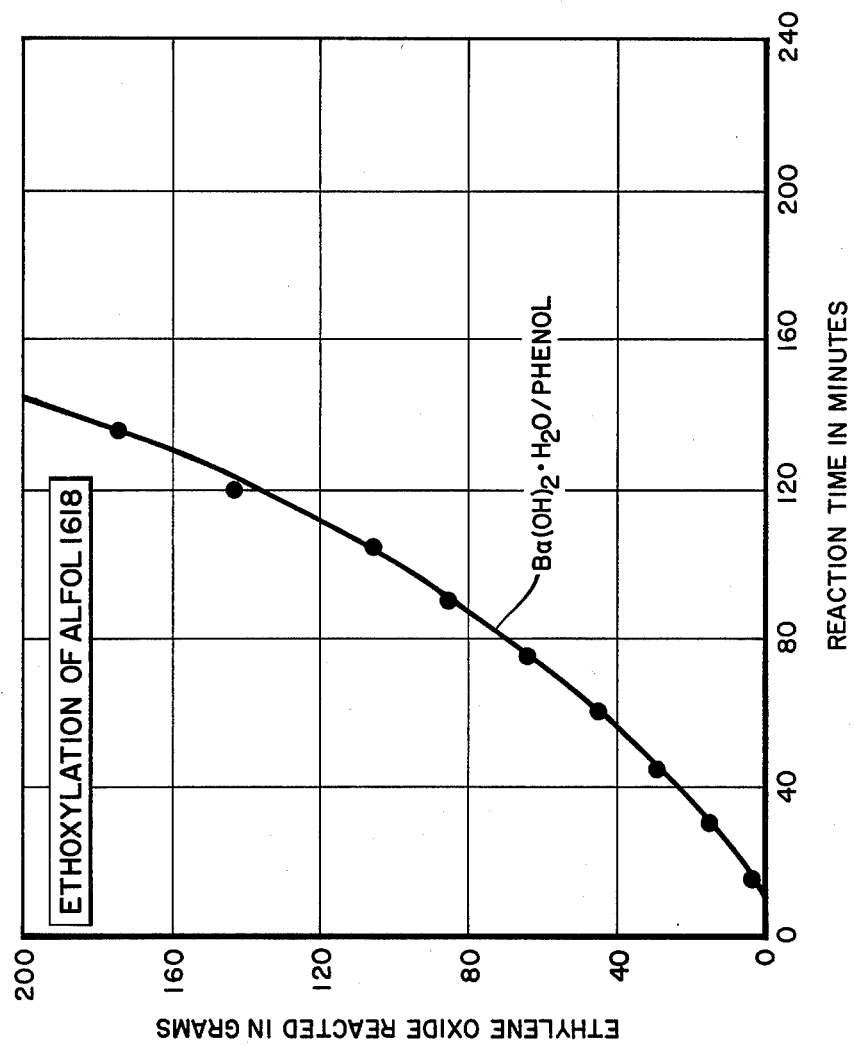

Example 5 was repeated using Alfol 1618 alcohol (trademark of and sold by Continental Oil Co.) and 0.5 grams phenol was added. FIG. 2, presented in the same fashion as FIG. 1, shows the reduced induction time before ethoxylation begins.

EXAMPLE 7

Figure 3:
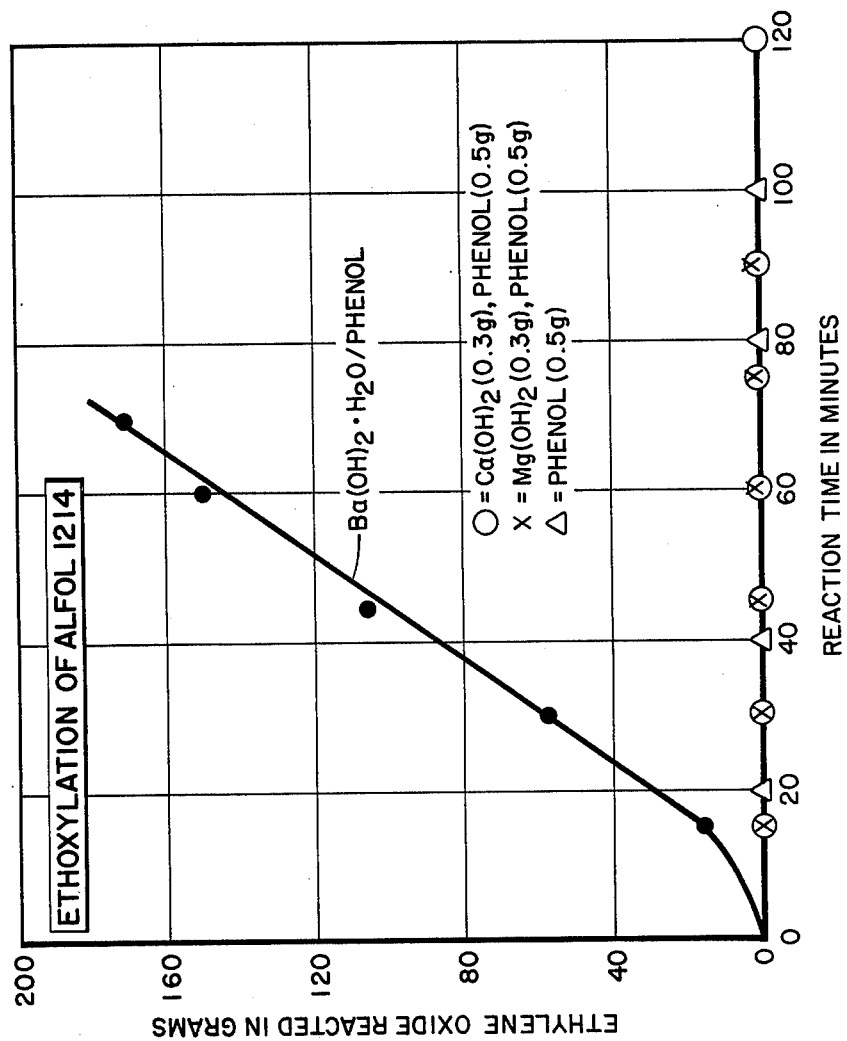

Example 1 was repeated exactly, using as comparators barium hydroxide, calcium hydroxide and magnesium hydroxide, each with phenol co-catalyst, as well as phenol alone. The relative effects of each of these catalyst systems are shown in FIG. 3, presented in the same format as FIGS. 1 and 2.

EXAMPLE 8

Example 1 was repeated using 0.2 grams NaOH in the absence of phenolic catalyst and the product was neutralized with $CO_2$. Reaction time was 60 minutes. The reaction product contained 0.15 weight percent glycol and 3.56 weight percent unreacted alcohol.

EXAMPLE 9

Example 8 was repeated using 0.2 grams NaOH and 1.0 gram phenol. Reaction time was 66 minutes and yielded a reaction product containing 0.14 weight percent glycol and 3.56 weight percent unreacted alcohol.

EXAMPLE 10

Example 8 was repeated with 0.2 grams of KOH. Reaction time was 83 minutes, yielding a reaction product containing 0.26 weight percent glycol and 2.8 weight percent unreacted alcohol.

EXAMPLE 11

Example 8 was repeated with 0.2 grams of KOH and 1.0 grams phenol. Reaction time was 79 minutes, and the reaction product contained 0.26 weight percent glycol and 2.5 weight percent unreated alcohol.

EXAMPLE 12

Figure 4:
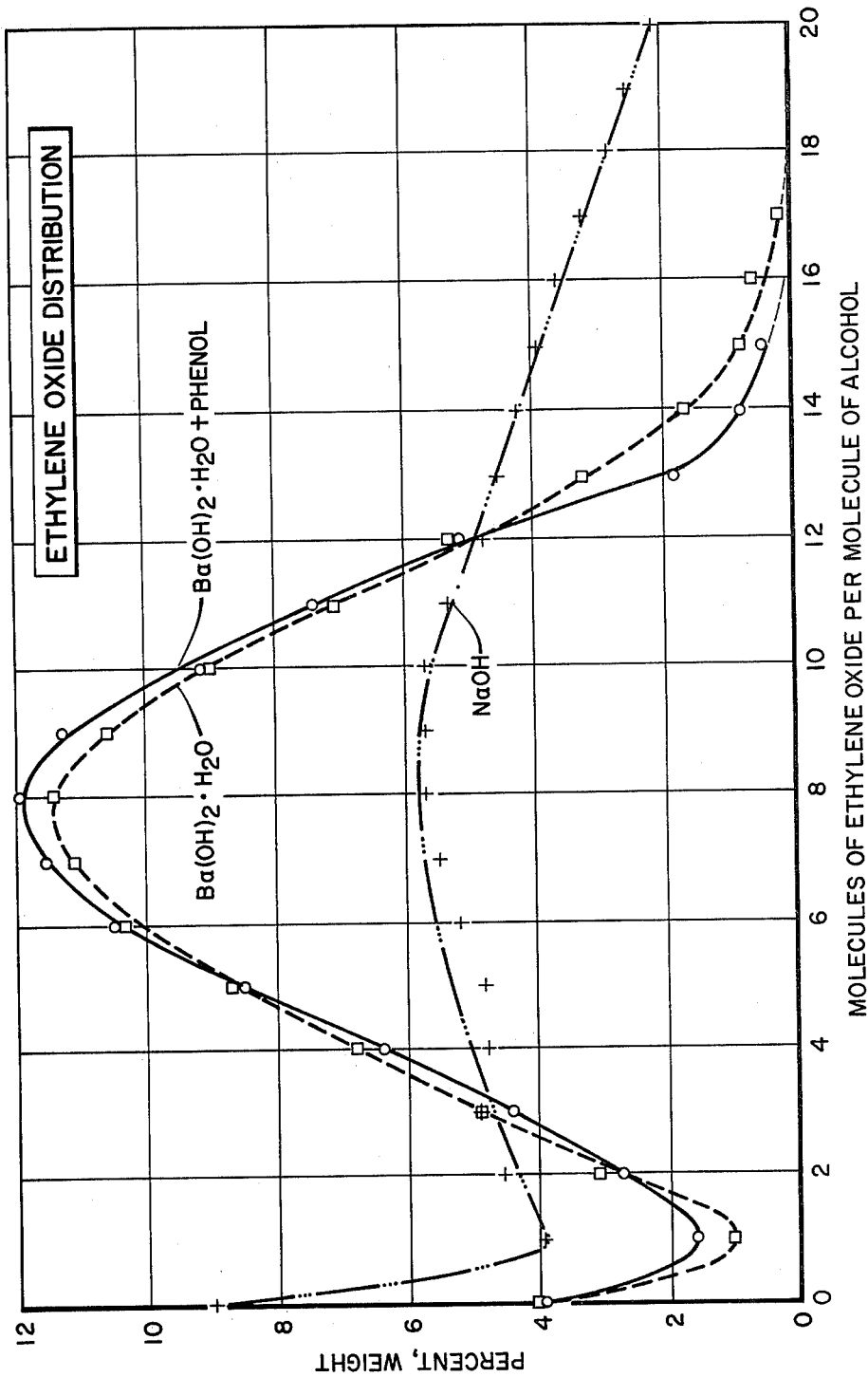

Example 1 was repeated using branched alcohol (2-butyl 1-octanol). Reaction time was 63 minutes. 43.75 grams of EO was consumed in the first 15 minutes of EO addition. The product had a pour point of 30° F. Glycol content was 0.52 weight percent and unreacted alcohol was 3.9 weight percent. EO distribution is shown in FIG. 4 where the vertical axis is weight percent based on total product, and the horizontal axis is moles of EO adduct per mole of alcohol. FIG. 4 shows EO weight percent distribution for 2-butyl-1-octanol, a branched alcohol.

EXAMPLE 13

Example 12 was repeated in the absence of co-catalyst. Reaction time was 84 minutes. Only 15.2 grams of EO was consumed in the first 15 minutes of EO addition. The product has a pour point of 35° F. Glycol content was 2.45 weight percent and unreacted alcohol was 4.0 weight percent. EO distribution is shown in FIG. 4.

EXAMPLE 14

For comparison, Example 12 was repeated using 0.15 grams NaOH catalyst. Neutralization of the catalyst was accomplished using acetic acid. Pour point of the product was 70° F. and unreacted alcohol was 8.9 weight percent. EO distribution is shown in FIG. 4.

It has also been discovered that the catalysts and method of the instant invention is extremely well suited for the ethoxylation of alcohols produced from olefins by hydroformylation (or oxo)/hydrogenation. Such alcohols have in the past presented difficulty when used as reactants for ethoxylation because of the high concentration of unreacted alcohols. However, the catalyst of the instant invention produces an extremely good ethoxylate using these alcohols.

Thus it is apparent that by practicing the instant invention, high mole adduct ethoxylates of alcohols can be obtained in a very narrow highly desirable distribution range while producing very low amounts of by-products and unreacted free alcohols while having a desirably fast reaction rate and greatly reducing or eliminating previously encountered induction periods.

Gas chromatographic (GLC) analysis of the experiments described, showed the basic barium containing catalysts of the instant invention to be low in by-product and unreacted free alcohols. The comparison with sodium hydroxide showed the barium oxide/cresylic acid catalyst system of the instant invention to favorably compare to the known basic catalyst. Both the barium/cresylic acid and sodium hydroxide ethoxylation products contained less than 1 parts per million (ppm) dioxane and less than 3 weight percent polyethylene glycols based on total reaction product and determined by solvent extraction. These basic catalysts produce reaction products far superior to those obtained with acid catalyzed ethoxylation, in which reaction products dioxane normally exceeds 1,000 parts per million and polyethylene glycol exceeds 3 weight percent.

Although exemplified as a batch reaction, the catalyst of the instant invention is also extremely well suited to continuous reaction methods, since the reaction products are extremely high desirable quality and quantity.

While certain embodiments and details have been shown for the purpose of illustrating this invention, it will be apparent to those skilled in this art that various changes and modifications may be made herein without departing from the spirit or scope of the invention.

We claim:

1. A method for the ethoxylation of alkanols containing from about 4 to about 24 carbon atoms comprising contacting said alkanols with ethylene oxide in the presence of a catalyst system comprising at least one material selected from the group consisting of barium oxide, barium hydroxide and hydrated barium hydroxide, together with an effective amount of phenol or a substituted phenol of the general formula

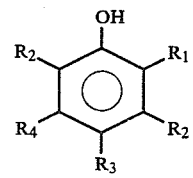

wherein $R_1$, $R_2$, $R_3$, $R_4$, and $R_5$ are independently hydrogen or an alkyl group containing from 1 to 10 carbon atoms, and wherein the ethoxylation is carried out at temperatures of from about 120° to about 250° C.

2. A method as described in claim 1 wherein the catalyst is selected from the group consisting of barium hydroxide and hydrated barium hydroxide.

3. A method as described in claim 1 wherein the alkanol to be ethoxylated contains from about 4 to about 20 carbon atoms.

4. A method as described in claim 3 wherein the alkanol is a primary alkanol.

5. A method as described in claim 3 wherein the alkanol is a product of a hydroformylation/hydrogenation reaction.

6. A method as described in claim 1 wherein the reaction is carried out at a pressure up to about 100 pounds per square inch gauge (psig).

7. A method as described in claim 6 wherein the ethylene oxide mole ratio adduct ranges from about 30 weight percent to about 80 weight percent of the ethoxylated product.

8. A method as described in claim 7 wherein the barium containing catalyst is present in an amount from about 0.1 to about 0.5% by weight based upon the alcohol to be reacted.

9. A method as described in claim 1 when carried out as a continuous reaction.

10. A method as described in claim 7 wherein the alkanol is a linear primary alkanol containing from about 8 to about 18 carbon atoms, the ethylene oxide is present in an amount of from about 40 to about 70%, temperature is about 180° C., the pressure is about 50 psig, and the barium containing catalyst is present in a concentration of from about 0.1 to about 0.5 percent based on the weight of the alcohol to be reacted together with an effective amount of phenol or substituted phenol.

* * * * *